US008609115B2

(12) United States Patent
Hassan et al.

(10) Patent No.: US 8,609,115 B2
(45) Date of Patent: Dec. 17, 2013

(54) HIGH SHEAR APPLICATION IN DRUG DELIVERY

(75) Inventors: Abbas Hassan, Sugar Land, TX (US); Rayford G. Anthony, College Station, TX (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 57 days.

(21) Appl. No.: 13/082,905

(22) Filed: Apr. 8, 2011

(65) Prior Publication Data

US 2011/0268659 A1 Nov. 3, 2011

Related U.S. Application Data

(60) Provisional application No. 61/330,104, filed on Apr. 30, 2010, provisional application No. 61/355,448, filed on Jun. 16, 2010.

(51) Int. Cl.
*A61K 9/00* (2006.01)

(52) U.S. Cl.
USPC .......................................................... 424/400

(58) Field of Classification Search
USPC .......................................................... 424/400
See application file for complete search history.

(56) References Cited

U.S. PATENT DOCUMENTS

| | | | |
|---|---|---|---|
| 3,887,167 A | 6/1975 | Irwin | |
| 5,538,191 A | 7/1996 | Holl | |
| 5,877,350 A | 3/1999 | Langer et al. | |
| 6,368,366 B1 | 4/2002 | Langer et al. | |
| 6,368,367 B1 | 4/2002 | Langer et al. | |
| 6,383,237 B1 | 5/2002 | Langer et al. | |
| 6,530,964 B2 | 3/2003 | Langer et al. | |
| 6,742,774 B2 | 6/2004 | Holl | |
| 2003/0043690 A1 | 3/2003 | Holl | |
| 2004/0052158 A1 | 3/2004 | Holl | |
| 2004/0187770 A1 | 9/2004 | Calabrese et al. | |
| 2005/0033069 A1 | 2/2005 | Holl et al. | |
| 2006/0245991 A1 | 11/2006 | Holl et al. | |
| 2007/0160577 A1 | 7/2007 | Damle et al. | |
| 2007/0160658 A1 | 7/2007 | Connor et al. | |
| 2008/0161588 A1 | 7/2008 | Hassan et al. | |
| 2009/0005592 A1 | 1/2009 | Hassan et al. | |
| 2009/0186088 A1 | 7/2009 | Chan et al. | |
| 2010/0008863 A1 | 1/2010 | Swenson et al. | |
| 2010/0035800 A1 | 2/2010 | Desai et al. | |
| 2010/0086490 A1 | 4/2010 | Allemann et al. | |
| 2012/0315308 A1* | 12/2012 | Travers | 424/400 |

FOREIGN PATENT DOCUMENTS

| | | |
|---|---|---|
| CN | 101068531 | 11/2007 |
| CN | 101312713 | 11/2008 |
| WO | 02064708 A2 | 8/2002 |

OTHER PUBLICATIONS

Junghanns et al., Int.l J. Nanomedicine 2008:3(3) 295-309.*
Aguilera et al., Food Materials Science, Principles and Practice (2008) Springer.*

Office Action dated Feb. 24, 2011 for U.S. Appl. No. 12/796,358.
Office Action dated Feb. 29, 2012 for U.S. Appl. No. 12/146,733.
Office Action dated Jun. 3, 2011 for U.S. Appl. No. 12/568,155.
Office Action dated Jun. 2, 2011 for U.S. Appl. No. 12/427,286.
Office Action dated Jun. 3, 2011 for U.S. Appl. No. 12/568,280.
International Search Report and Written Opinion dated Feb. 8, 2012 for corresponding PCT Application No. PCT/US2011/031725 (9 pgs).
International Search Report and Written Opinion dated Feb. 17, 2012 for corresponding PCT Application No. PCT/US2011/031727(11 pgs).
"Cavitation: A technology on the horizon," Current Science 91 (No. 1): 35-46 (2006).
IKA—Rotor-Stator Generators—2003 Processing Catalog (38 pgs.).
Office Action dated Apr. 20, 2010 for U.S. Appl. No. 12/411,660.
Office Action dated Apr. 20, 2010 for U.S. Appl. No. 12/427,286.
Office Action dated Apr. 23, 2010 for U.S. Appl. No. 12/568,155.
Office Action dated Apr. 27, 2010 for U.S. Appl. No. 12/568,280.
Office Action dated May 5, 2010 for U.S. Appl. No. 12/142,120.
Office Action dated Jun. 25, 2009 for U.S. Appl. No. 12/142,447.
Office Action dated Jan. 7, 2010 for U.S. Appl. No. 12/142,447.
Office Action dated May 13, 2010 for U.S. Appl. No. 12/142,447.
Office Action dated Feb. 4, 2010 for U.S. Appl. No. 12/492,721.
Office Action dated Feb. 18, 2010 for U.S. Appl. No. 12/635,433.
Office Action dated Feb. 18, 2010 for U.S. Appl. No. 12/635,454.
Office Action dated May 14, 2010 for U.S. Appl. No. 12/137,441.
Office Action dated Feb. 19, 2010 for U.S. Appl. No. 12/144,459.
Office Action dated Sep. 2, 2009 for U.S. Appl. No. 12/142,433.
Office Action dated Jan. 29, 2010 for U.S. Appl. No. 12/142,433.
Office Action dated May 24, 2010 for U.S. Appl. No. 12/142,433.
Office Action dated Apr. 30, 2010 for U.S. Appl. No. 12/141,191.
Office Action dated Oct. 27, 2009 for U.S. Appl. No. 12/142,120.
Office Action dated May 5, 2010 for U.S. Appl. No. 12/571,537.
Office Action dated Jul. 28, 2010 for U.S. Appl. No. 12/635,433.
Australian Examination Report dated Feb. 18, 2013 for corresponding Australian Application No. 2011248866 (3 pgs.).
IKA—Single Stage Shear Pumps: Ultra Turax UTL 2000-2003 Processing Ctalog (2 pgs.).
IKA—DRS Reactors website http://www.ikausa.com/dr.him, on Sep. 8, 2010 (2 pgs.).

(Continued)

*Primary Examiner* — Michael G Hartley
*Assistant Examiner* — Robert Cabral
(74) *Attorney, Agent, or Firm* — Timothy S. Westby; Porter Hedges, LLP (57) ABSTRACT

In this disclosure, methods and systems for drug delivery utilizing high shear are disclosed. In an embodiment, a method comprises (1) subjecting a therapeutic fluid containing a drug to high shear; and (2) obtaining a processed therapeutic fluid, wherein the processed therapeutic fluid contains the drug in nano-size. In an embodiment, a method comprises (1) subjecting a drug carrier and a therapeutic fluid containing a drug to high shear; and (2) obtaining a processed therapeutic fluid, wherein the processed therapeutic fluid contains the drug carrier loaded with the drug. In an embodiment, a method comprises (1) applying high shear to a drug carrier and a therapeutic fluid containing a drug; (2) obtaining a processed therapeutic fluid, wherein the processed therapeutic fluid contains the drug-loaded carrier; and (3) modifying the drug-loaded carrier with a targeting moiety to obtain a modified drug-loaded carrier.

18 Claims, 7 Drawing Sheets

(56) References Cited

OTHER PUBLICATIONS

IKA, "Introduction to IKA's Three Stage Dispax Reactor," Retrieved from <http://www.ikausa.com/pdfs/process/dr% 202000-Homogenizing-Dispersing-Suspending-Emulsifying.pdf> on Aug. 22, 2012 (12 pgs.).

International Preliminary Report on Patentability dated Nov. 6, 2012 for corresponding International Application No. PCT/US2011/031727 (5 pgs.).

Benavides et al., "Hydrogen Sulfide Mediates the Vasoactivity of Garlic," Proceedings of the National Academy of Sciences, dated Nov. 13, 2007, vol. 104, No. 46, pp. 17977-17982 (6 pgs.).

Australian Office Action dated Apr. 22, 2013 for corresponding Australian Application No. 2011248867 (4 pgs.).

Chattopadhyay et al., "Understanding Mechanical Energy Driven Nonequilibrium Processing: Some Results, Eleventh International Conference on Rapidly Quenched and Metastable Materials," A Material Science and Engineering, vol. 375-377, dated Jul. 15, 2004, pp. 72-77 (9 pgs.).

Canadian Office Action dated Aug. 7, 2013 for corresponding Canadian Application No. 2,798,049 (2 pgs.).

Chinese Office Action dated May 28, 2013 for corresponding Chinese Application No. 201180021836.4 (10 pgs.).

\* cited by examiner

HIGH SHEAR APPLICATION IN DRUG DELIVERY

CROSS-REFERENCE TO RELATED APPLICATIONS

This application claims the benefit under 35 U.S.C. §119 (e) of U.S. Provisional Patent Application Nos. 61/330,104 filed Apr. 30, 2010 and 61/355,448 filed Jun. 16, 2010, the disclosure of said applications is hereby incorporated herein by reference.

FIELD OF THE INVENTION

The present invention generally relates to drug delivery. More particularly, the present invention relates to utilizing a shear device to apply suitable shear stress to therapeutic fluids for drug delivery.

BACKGROUND

Drug delivery is the method or process of administering a pharmaceutical compound to achieve a therapeutic effect in humans or animals. Different delivery mechanisms may alter drug release profile, absorption, distribution, and elimination for the benefit of improving product efficacy and safety, as well as patient convenience and compliance. Most common methods of delivery include the preferred non-invasive per-oral (through the mouth), topical (skin), transmucosal (nasal, buccal/sublingual, vaginal, ocular and rectal), and inhalation routes. Injection or infusion is used to deliver medications such as peptides, proteins, antibodies, vaccines, and gene based drugs because such medications are generally susceptible to enzymatic degradation or are unable to be absorbed into the systemic circulation efficiently due to their molecular size and charge for therapeutic efficacy. For example, many immunizations are based on the delivery of protein drugs and are often done by injection.

Targeted drug delivery or targeted delivery is one of the areas in drug delivery that has drawn immense attention. The basic concept is to develop delivery mechanisms that cause the drug to be active only in a particular target area of the body (for example, in cancerous tissues). Sustained release formulation is another area in which the drug is released over a period of time in a controlled manner from a formulation. Sustained release formulations often include the use of liposomes, biodegradable microspheres, and drug-polymer conjugates.

Drug delivery remains one of the most complex, intriguing, and exciting research areas in industry, medicine, science, and technology. Therefore there is an ongoing need and interest to develop new methods and systems to improve drug delivery in various aspects.

SUMMARY

In an embodiment, a method is disclosed. The method comprises (1) subjecting a therapeutic fluid containing a drug to high shear; and (2) obtaining a processed therapeutic fluid, wherein the processed therapeutic fluid contains the drug in nano-size. In various embodiments, the drug is in the form of a solid, liquid, gas, solution, gel, emulsion, powder, or a combination thereof. In some embodiments, the method further comprises controlling the shear rate that the therapeutic fluid is subjected to high shear. In some embodiments, the method further comprises controlling the period of time that the therapeutic fluid is subjected to high shear. In some embodiments, the drug in nano-size has improved efficacy when administered to a patient. In some embodiments, subjecting the therapeutic fluid containing the drug to high shear comprises creating free radicals of the drug.

In an embodiment, a method is described. The method comprises (1) subjecting a drug carrier and a therapeutic fluid containing a drug to high shear; and (2) obtaining a processed therapeutic fluid, wherein the processed therapeutic fluid contains the drug carrier loaded with the drug. In some embodiments, the method further comprises administering the processed therapeutic fluid to a patient. In some embodiments, subjecting the drug carrier and the therapeutic fluid containing the drug to high shear creates an interaction between the drug carrier and the drug or enhances the interaction between the drug carrier and the drug. In some embodiments, subjecting the drug carrier and the therapeutic fluid containing the drug to high shear improves the loading capacity of the drug carrier for the drug.

In an embodiment, a method is disclosed. The method comprises (1) applying high shear to a drug carrier and a therapeutic fluid containing a drug; (2) obtaining a processed therapeutic fluid, wherein the processed therapeutic fluid contains the drug-loaded carrier; and (3) modifying the drug-loaded carrier with a targeting moiety to obtain a modified drug-loaded carrier. In some embodiments, the method further comprises concentrating the processed therapeutic fluid containing the drug-loaded carrier. In some embodiments, the method further comprises purifying the drug-loaded carrier from the processed therapeutic fluid. In some embodiments, the method further comprises administering the modified drug-loaded carrier to a patient. In some cases, the modified drug-loaded carrier is used to treat cancer patients.

In an embodiment, a system is described. The system comprises (1) a high shear device; and (2) a pump configured to control the flow rate and residence time of a fluid passing through the high shear device. In various embodiments, the fluid passage of the system is sterile. In some embodiments, the system further comprises at least one temperature control unit configured to control the temperature of the high shear device. In some embodiments, the system further comprises at least one storage vessel in fluid communication with the high shear device. In some embodiments, the system further comprises at least one device configured for intravenous administration of the fluid to a patient.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a more detailed description of the preferred embodiment of the present invention, reference will now be made to the accompanying drawings, wherein.

NOTATION AND NOMENCLATURE

As used herein, the term "therapeutic fluids" refers to dispersions that contain at least one substance that has therapeutic effects (i.e., drug). Some examples of these substances are neurological drugs, anti-inflammatory drugs, anti-cancer drugs, antibiotics, therapeutic gases (e.g., ozone, sulfur based gases, carbon monoxide, oxygen, hydrogen), viral vectors, genes, proteins, polymers, liposomes, organic particles, inorganic particles (e.g. minerals). Such substances/drugs may be a gas, a liquid, a gel, or a solid.

As used herein, the term "dispersion" refers to a liquefied mixture that contains at least two distinguishable substances (or "phases") that either will or will not readily mix and dissolve together. As used herein, a "dispersion" comprises a "continuous" phase (or "matrix"), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is miscible or immiscible, and continuous liquid phases throughout which solid particles are distributed. As used herein, the term "dispersion" encompasses continuous liquid phases throughout which gas bubbles are distributed, continuous liquid phases throughout which solid particles are distributed, continuous phases of a first liquid throughout which droplets of a second liquid that is soluble or insoluble in the continuous phase are distributed, and liquid phases throughout which any one or a combination of solid particles, miscible/immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination.

Certain terms are used throughout the following description and claims to refer to particular system components. This document does not intend to distinguish between components that differ in name but not function.

In the following description and in the claims, the terms "including" and "comprising" are used in an open-ended fashion, and thus should be interpreted to mean "including, but not limited to . . . ".

DETAILED DESCRIPTION

Shear Device

Shear device is a mechanical device that utilizes one or more generator comprising a rotor/stator combination, each of which has a gap between the stator and rotor. The gap between the rotor and the stator in each generator set may be fixed or may be adjustable. Shear device is configured in such a way that it is capable of producing submicron and micron-sized bubbles or nano-size particles in a mixture flowing through the high shear device. The high shear device comprises an enclosure or housing so that the pressure and temperature of the mixture may be controlled.

High shear mixing devices are generally divided into three general classes, based upon their ability of mixing/dispersing. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the submicron to about 1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.0254 mm to 10.16 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (meters, for example) times the frequency of revolution (for example revolutions per minute, rpm). A colloid mill, for example, may have a tip speed in excess of 22.9 m/s (4500 ft/min) and may exceed 40 m/s (7900 ft/min). For the purpose of this disclosure, the term 'high shear' refers to mechanical rotor stator devices (e.g., colloid mills or rotor-stator dispersers) that are capable of tip speeds in excess of 5.1 m/s. (1000 ft/min) and require an external mechanically driven power device to drive energy into the feed stream to be processed. For example, in a shear device, a tip speed in excess of 22.9 m/s (4500 ft/min) is achievable, and may exceed 40 m/s (7900 ft/min). In some embodiments, a shear device is capable of delivering at least 300 L/h at a tip speed of at least 22.9 m/s (4500 ft/min) The power consumption will vary depending on the viscosity, temperature and pressure of operation. Shear device combines high tip speed with a very small shear gap to produce significant shear on the material being processed. The amount of shear will be dependent on the viscosity of the fluid. Accordingly, a local region of elevated pressure and temperature is created at the tip of the rotor during operation of the high shear device. In some cases the locally elevated pressure is about 1034.2 MPa (150,000 psi). In some cases the locally elevated temperature is about 500° C. In some cases, these local pressure and temperature elevations may persist for nano or pico seconds.

Without wishing to be limited to a particular theory, it is believed that the level or degree of high shear mixing is sufficient to produce localized non-ideal conditions. Localized non-ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the feed stream components into free radicals, which may intensify an interaction (e.g., a chemical reaction) or allow an interaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006).

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the feed stream components. In embodiments, the energy expenditure of shear device is greater than 1000 W/m$^3$. In embodiments, the energy expenditure of shear device is in the range of from about 3000 W/m$^3$ to about 7500 W/m$^3$.

The shear rate is the tip speed divided by the shear gap width (minimal clearance between the rotor and stator). The shear rate generated in a shear device may be in the greater than 20,000 s$^{-1}$. In some embodiments the shear rate is at least 40,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In embodiments, the shear rate generated by a shear device is in the range of from 20,000 s$^{-1}$ to 100,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$. In some embodiments, shear device comprises a colloid mill. Suitable colloidal mills are manufactured by IKA® Works, Inc. Wilmington, N.C. and APV North America, Inc. Wilmington, Mass., for example. In some instances, shear device comprises the Dispax Reactor® of IKA® Works, Inc.

The high shear device comprises at least one revolving element that creates the mechanical force applied to the stream that passes through. The high shear device comprises at least one stator and at least one rotor separated by a clearance. For example, the rotors may be conical or disk shaped and may be separated from a complementarily-shaped stator. In embodiments, both the rotor and stator comprise a plurality of circumferentially-spaced teeth. In some embodiments, the stator(s) are adjustable to obtain the desired shear gap between the rotor and the stator of each generator (rotor/stator set). Grooves between the teeth of the rotor and/or stator may alternate direction in alternate stages for increased turbulence. Each generator may be driven by any suitable drive system configured for providing the necessary rotation.

In some embodiments, the minimum clearance (shear gap width) between the stator and the rotor is in the range of from about 0.0254 mm (0.001 inch) to about 3.175 mm (0.125 inch). In certain embodiments, the minimum clearance (shear gap width) between the stator and rotor is about 1.52 mm (0.060 inch). In certain configurations, the minimum clearance (shear gap) between the rotor and stator is at least 1.78 mm (0.07 inch). The shear rate produced by the high shear device may vary with longitudinal position along the flow pathway. In some embodiments, the rotor is set to rotate at a speed commensurate with the diameter of the rotor and the desired tip speed. In some embodiments, the high shear device has a fixed clearance (shear gap width) between the stator and rotor. Alternatively, the high shear device has adjustable clearance (shear gap width).

In some embodiments, a shear device comprises a single stage dispersing chamber (i.e., a single rotor/stator combination, a single generator). In some embodiments, a shear device is a multiple stage inline disperser and comprises a plurality of generators. In certain embodiments, a shear device comprises at least two generators. In other embodiments, a shear device comprises at least 3 high shear generators. In some embodiments, a shear device is a multistage mixer whereby the shear rate (which, as mentioned above, varies proportionately with tip speed and inversely with rotor/stator gap width) varies with longitudinal position along the flow pathway, as further described herein below.

In some embodiments, each stage of the shear device has interchangeable mixing tools, offering flexibility. For example, the DR 2000/4 Dispax Reactor® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of dispersions having a narrow distribution of the desired bubble size and particle size. In some embodiments, each of the stages is operated with super-fine generator. In some embodiments, at least one of the generator sets has a rotor/stator minimum clearance (shear gap width) of greater than about 5.0 mm (0.20 inch). In alternative embodiments, at least one of the generator sets has a minimum rotor/stator clearance of greater than about 1.78 mm (0.07 inch).

Figure 1A:
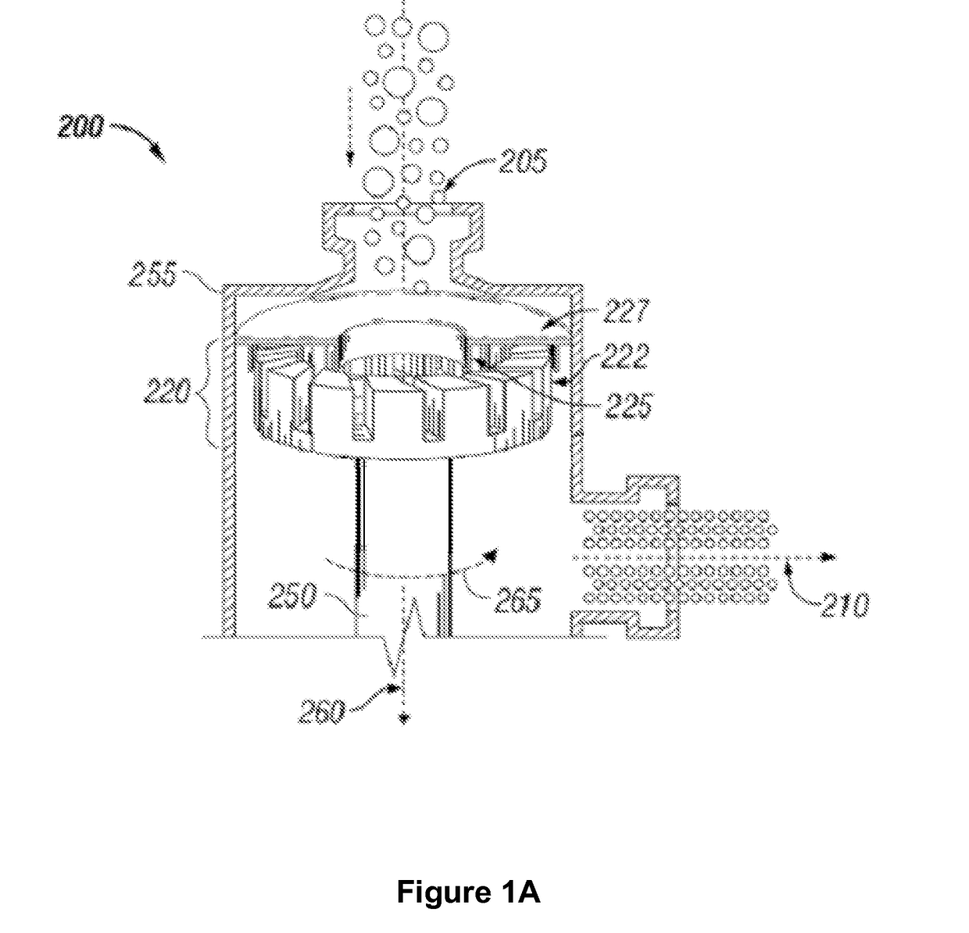
FIG. 1A is a longitudinal cross-section view of a one-stage shear device.

FIG. 1A presents a longitudinal cross-section of a suitable shear device 200. Shear device 200 of FIG. 1A is a dispersing device comprising a combination 220 of a rotor 222 and a stator 227. The rotor-stator combination may be known as generator 220 or stage without limitation. The rotor 222 and stator 227 are fitted along drive shaft 250.

For generator 220, the rotor 222 is rotatably driven by input 250 and rotates about axis 260 as indicated by arrow 265. The direction of rotation may be opposite that shown by arrow 265 (e.g., clockwise or counterclockwise about axis of rotation 260). Stator 227 is fixably coupled to the wall 255 of shear device 200. Generator 220 has a shear gap width which is the minimum distance between the rotor and the stator. In the embodiment of FIG. 1A, generator 220 comprises a shear gap 225.

Generator 220 may comprise a coarse, medium, fine, and super-fine characterization. Rotors 222 and stators 227 may be toothed designs. Generator 220 may comprise two or more sets of rotor-stator teeth. In embodiments, rotor 222 comprises rotor teeth circumferentially spaced about the circumference of the rotor. In embodiments, stator 227 comprises stator teeth circumferentially spaced about the circumference of the stator.

Shear device 200 is configured for receiving fluid mixtures at inlet 205. Fluid mixtures entering inlet 205 are pumped serially through generator 220, such that product dispersions are formed. Product dispersions exit shear device 200 via outlet 210. Rotor 222 of generator 220 rotates at a speed relative to the fixed stator 227, providing adjustable shear rates. The rotation of the rotor pumps fluid, such as the fluid mixtures entering inlet 205, outwardly through the shear gaps (and, if present, through the spaces between the rotor teeth and the spaces between the stator teeth), creating a localized shear condition. Shear forces exerted on fluid in shear gap 225 (and, when present, in the gaps between the rotor teeth and the stator teeth) through which fluid flows process the fluid and create product dispersion. Product dispersion exits shear device 200 via shear outlet 210.

In certain instances, shear device 200 comprises a ULTRA-TURRAX® of IKA® Works, Inc. Wilmington, N.C. Several models are available having variable sizes, volume capacities, flow rates, tip speeds, inlet/outlet connections, horsepower, output rpm, and operable temperature ranges. For example, the T 10 basic ULTRA-TURRAX® homogenizer provides a stepless control of speed with a speed range of 8000-30000 $min^{-1}$ and adjustable dispersing elements.

In certain embodiments, more than one stage or combination of rotor and stator may be employed. example, two or three stages of rotor-stator combinations are connected serially along the same drive shaft to enable flexibility to provide variable shear stress. Fluid mixtures are passed through different stages of rotor-stator combinations to be processed serially until the desired dispersion products are formed. Examples of adjustable operational parameters are rotor size, stator size, shear gap, rotor speed, tip speed, shear rate, flow rate, residence time.

Figure 1B:
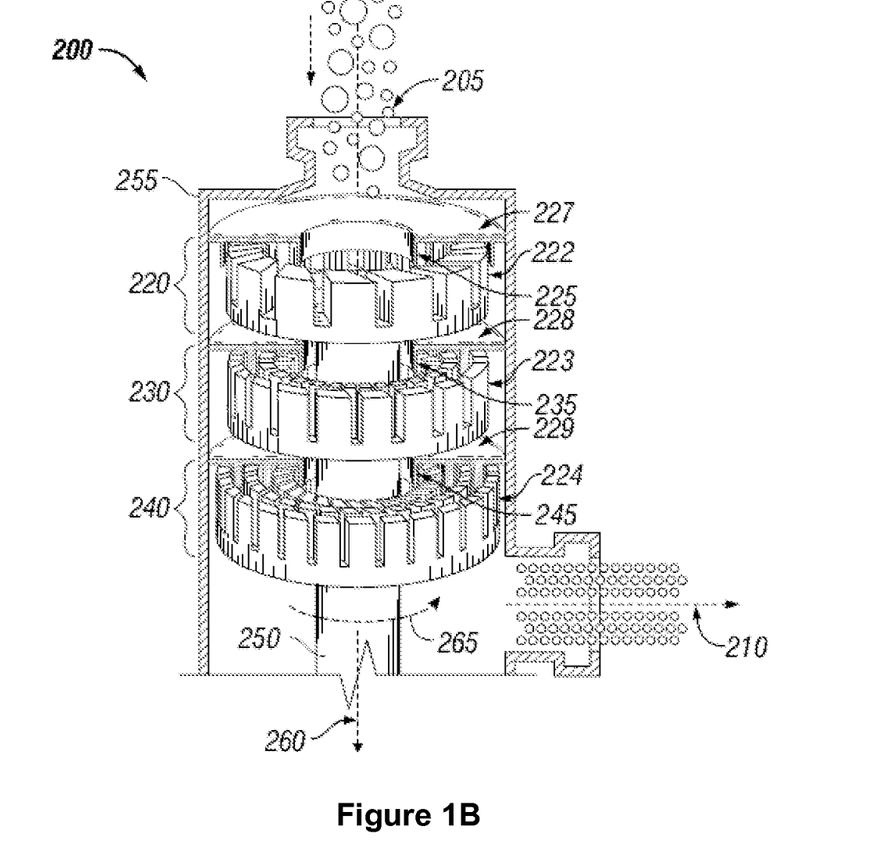
FIG. 1B is a longitudinal cross-section view of a three-stage shear device.

FIG. 1B presents a longitudinal cross-section of a three-stage shear device 200, comprising three stages or rotor-stator combinations 220, 230, and 240 as a dispersing device. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 are fixably coupled to the wall 255 of high shear device 200.

As mentioned hereinabove, each generator has a shear gap width which is the minimum distance between the rotor and the stator. In the embodiment of FIG. 1B, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10.0 mm. Alternatively, the process comprises utilization of a high shear device 200 wherein the gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. High shear device 200 may be configured so that the shear rate will increase stepwise longitudinally along the direction of the flow 260.

Generators 220, 230, and 240 may comprise a coarse, medium, fine, and super-fine characterization. Rotors 222, 223, and 224 and stators 227, 228, and 229 may be toothed designs. Each generator may comprise two or more sets of rotor-stator teeth. In embodiments, rotors 222, 223, and 224 comprise more than 10 rotor teeth circumferentially spaced about the circumference of each rotor. In embodiments, stators 227, 228, and 229 comprise more than ten stator teeth circumferentially spaced about the circumference of each stator. In embodiments, the inner diameter of the rotor is about 12 cm. In embodiments, the diameter of the rotor is about 6 cm. In embodiments, the outer diameter of the stator is about 15 cm. In embodiments, the diameter of the stator is about 6.4 cm. In some embodiments the rotors are 60 mm and the stators are 64 mm in diameter, providing a clearance of about 4 mm In certain embodiments, each of three stages is operated with a super-fine generator, comprising a shear gap of between about 0.025 mm and about 4 mm. For applications in which solid particles are to be sent through high shear device 40, the appropriate shear gap width (minimum clearance between rotor and stator) may be selected for an appropriate reduction in particle size and increase in particle surface area. In embodiments, this may be beneficial for increasing surface area of solid drugs by shearing and dispersing the particles.

High shear device 200 is configured for receiving a feed stream at inlet 205. Feed stream entering inlet 205 is pumped serially through generators 220, 230, and then 240, such that a dispersion is formed. The dispersion exits high shear device 200 via outlet 210. The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create the dispersion. The product dispersion exits high shear device 200 via high shear outlet 210.

The produced dispersion has an average gas bubble size less than about 5 µm. In embodiments, shear device 200 produces a dispersion having a mean bubble size of less than about 1.5 µm. In embodiments, shear device 200 produces a dispersion having a mean bubble size of less than 1 µm; preferably the bubbles are sub-micron in diameter. In certain instances, the average bubble size is from about 0.1 µm to about 1.0 µm. In embodiments, shear device 200 produces a dispersion having a mean bubble size of less than 400 nm. In embodiments, shear device 200 produces a dispersion having a mean bubble size of less than 100 nm. Shear device 200 produces a dispersion comprising dispersed gas bubbles capable of remaining dispersed at atmospheric pressure for at least about 15 minutes.

In certain instances, high shear device 200 comprises a Dispax Reactor® of IKA® Works, Inc. Wilmington, N.C. and APV North America, Inc. Wilmington, Mass. Several models are available having various inlet/outlet connections, horsepower, tip speeds, output rpm, and flow rate. Selection of the high shear device will depend on throughput requirements and desired particle or bubble size in dispersion exiting outlet 210 of high shear device 200. IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2HP power, output speed of 7900 rpm, flow capacity (water) approximately 300-700 L/h (depending on generator), a tip speed of from 9.4-41 m/s (1850 ft/min to 8070 ft/min).

Application of Shear in Drug Delivery

Figure 2A:
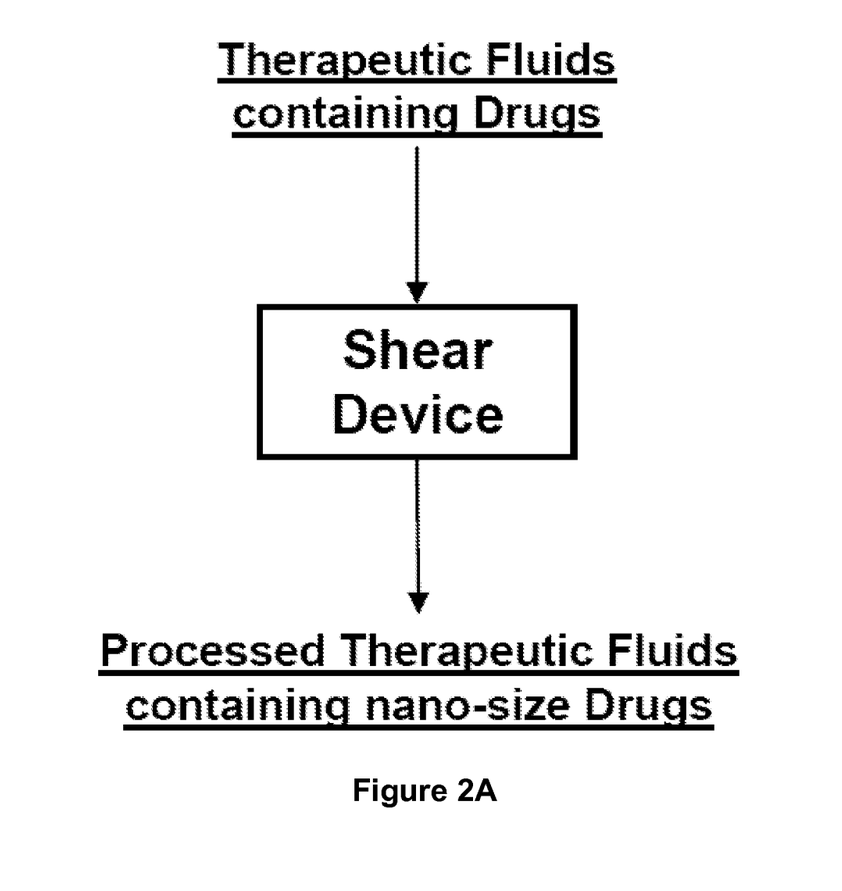
FIG. 2A illustrates a method of utilizing a shear device for drug delivery.
Figure 3A:
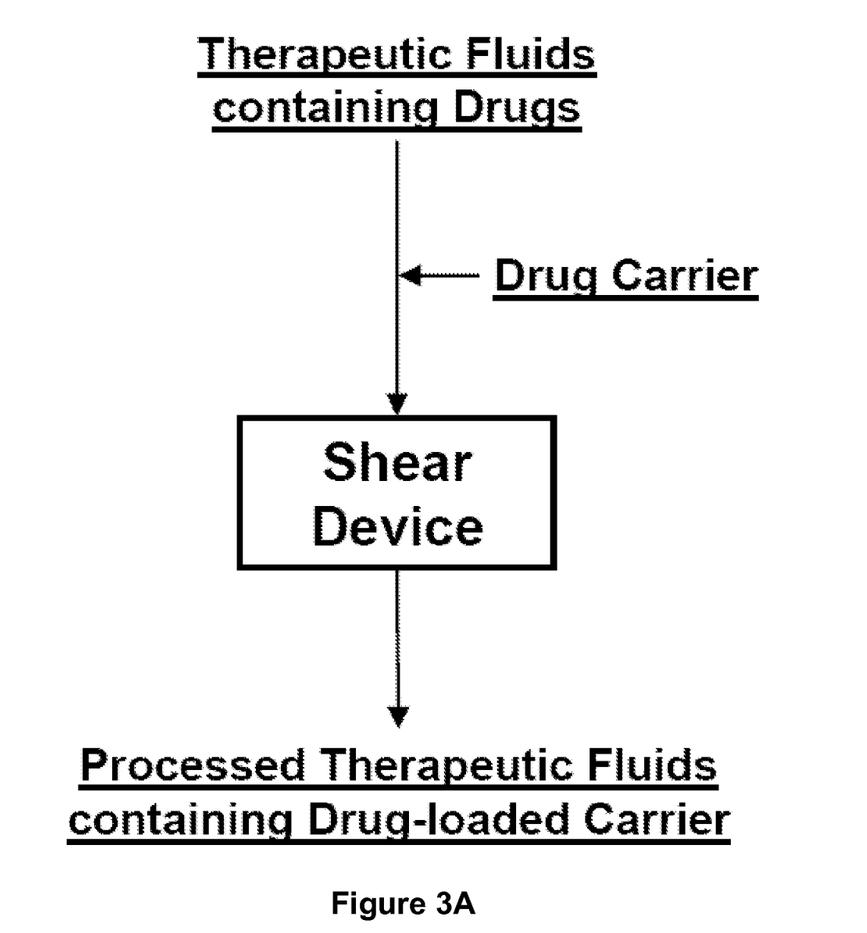
FIG. 3A illustrates a method of utilizing a shear device in conjunction with a drug carrier for drug delivery.
Figure 4A:
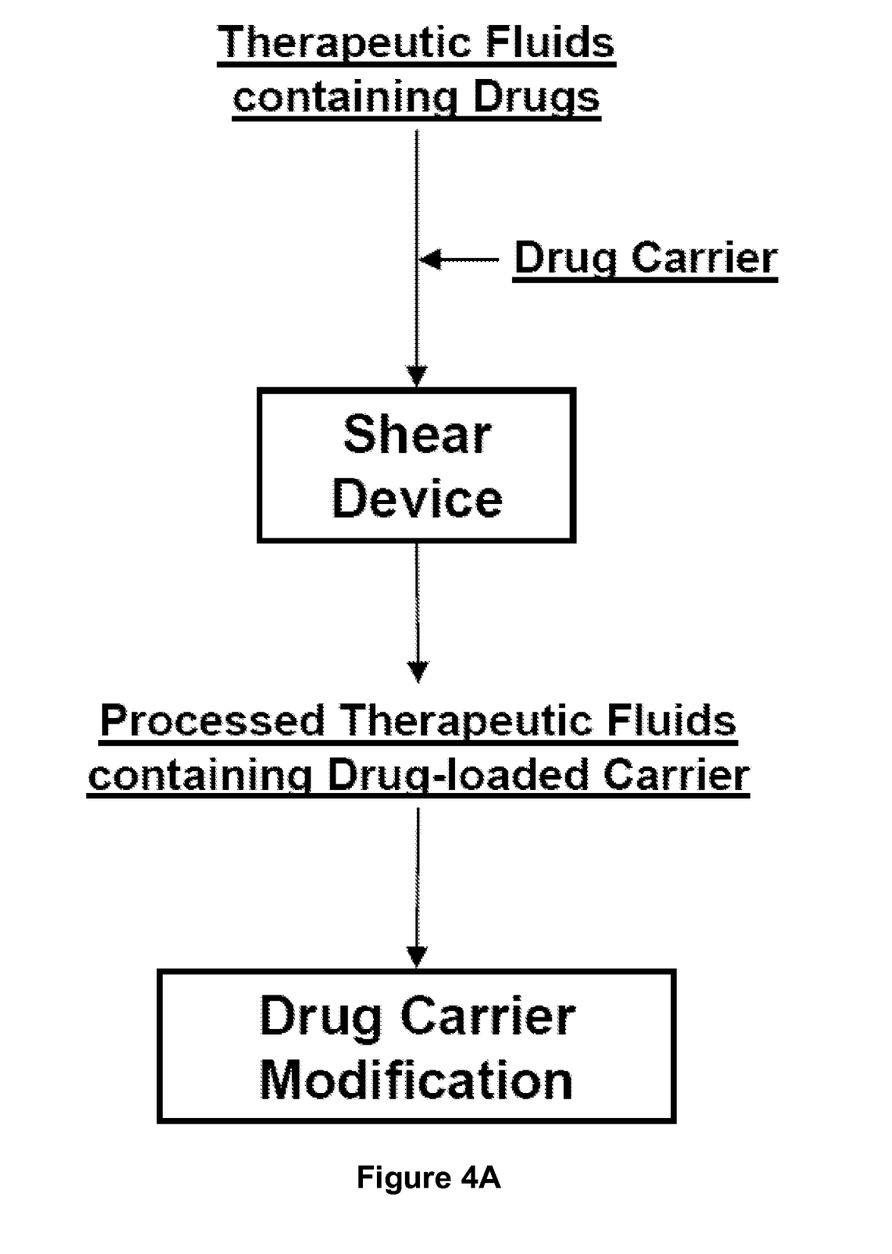
FIG. 4A illustrates a method of utilizing a shear device in conjunction with a drug carrier and drug carrier modification for drug delivery.

In an embodiment, the application of shear comprises passing a drug-containing therapeutic fluid through a shear device as described herein, wherein said drug is processed into its nano-size equivalent, as illustrated by FIG. 2A. As used herein, "nano-size" refers to the size range of sub-nanometers to 1000 nanometers. In an embodiment, the application of shear comprises passing a drug-containing therapeutic fluid and a drug carrier through a shear device, wherein the drug carrier is loaded with the drug after the shearing process, as illustrated by FIG. 3A. In an embodiment, the application of shear comprises passing a drug-containing therapeutic fluid and a drug carrier through a shear device, wherein the drug carrier is loaded with the drug; and modifying the drug-loaded carrier; as illustrated by FIG. 4A. In various embodiments, fluid passage is sterilized and is maintained sterile.

Nano-Size Drugs

In an embodiment, as illustrated by FIG. 2A, a therapeutic fluid containing a drug is processed by a shear device. The drug contained therein is subjected to a suitable shear rate for a period of time so that the processed therapeutic fluid after exiting the shear device contains the nano-size equivalent of the drug.

The shear rate generated in high shear device (HSD) may be in the greater than 20,000 $s^{-1}$. In some embodiments the shear rate is at least 40,000 $s^{-1}$. In some embodiments the shear rate is at least 100,000 $s^{-1}$. In some embodiments the shear rate is at least 500,000 $s^{-1}$. In some embodiments the shear rate is at least 1,000,000 $s-1$. In some embodiments the shear rate is at least 1,600,000 $s^{-1}$. In embodiments, the shear rate generated by HSD is in the range of from 20,000 $s-1$ to 100,000 $s^{-1}$. For example, in one application the rotor tip speed is about 40 m/s (7900 ft/min) and the shear gap width is 0.0254 mm (0.001 inch), producing a shear rate of 1,600,000 $s-1$. In another application the rotor tip speed is about 22.9 m/s (4500 ft/min) and the shear gap width is 0.0254 mm (0.001 inch), producing a shear rate of about 901,600 $s^{-1}$.

In some embodiments, the processed therapeutic fluid is immediately administered to a patient via any suitable means known to one skilled in the art. In some other embodiments, the processed therapeutic fluid is stored. In some further embodiments, the processed therapeutic fluid is further processed.

Selection of the shear device, shear rate, shear stress, and residence time applied in shear device depends on the amount of therapeutic fluid/dispersion administered and the nature of the components of the therapeutic fluids utilized. The operational parameters are further adjusted according to the objectives of tasks at hand, which dictate the specific requirements for the therapeutic fluids. For example, the dispersion of gases and liquids in a continuous phase may take place at a lower rate and/or for a shorter time than in the case of the dispersion of solids.

In some embodiments, shear is applied to therapeutic fluids to treat diseases such as cancers and brain diseases. In alternative embodiments, shear is applied to therapeutic fluids to treat diseases according to one's interest and the use of available drugs.

Figure 2B:
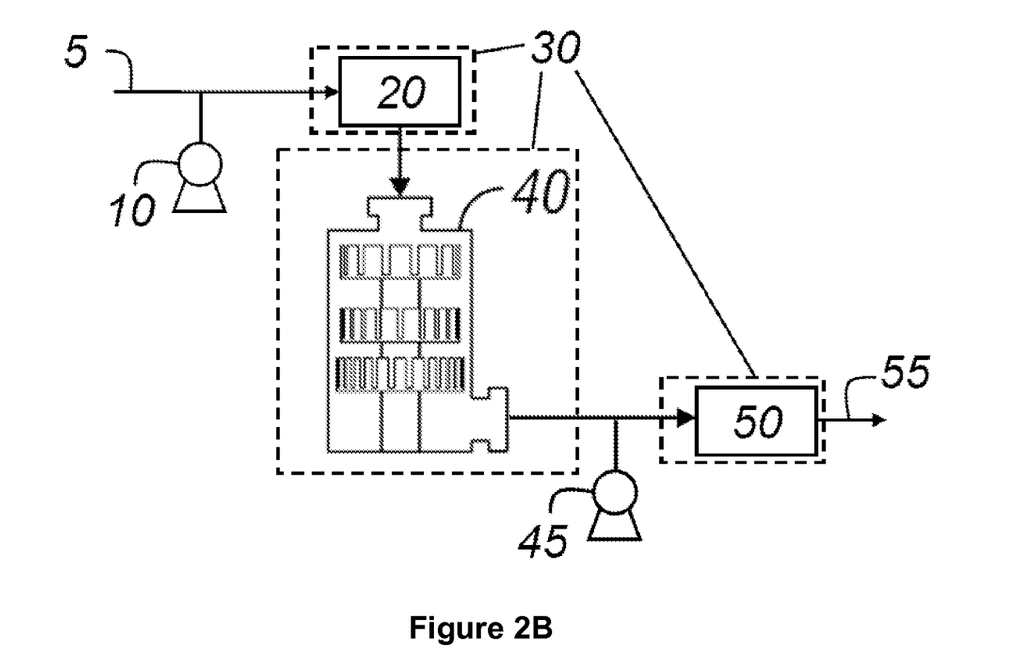
FIG. 2B is a process flow diagram demonstrating the application of shear stress for drug delivery.

Referring to FIG. 2B, a therapeutic fluid 5 containing a drug are transported and stored in a vessel 20 with a temperature control unit 30. Alternatively, the creation of therapeutic fluid 5 is achieved by any other suitable method known to one skilled in the art. The temperature control unit 30 is any device known to one skilled in the art and has the capacity to maintain a temperature between 0-100° C. within ±2° C. fluctuations. In some embodiments, a pump 10 is included to control the flow into vessel 20. Pump 10 is configured for either continuous or semi-continuous operation, and may be any suitable pumping device. Vessel 20 is configured to be in fluid connection with shear device 40 (at inlet 205 in FIGS. 1A and 1B), wherein said fluid connection may be any as known to one skilled in the art. The temperature of shear device 40 is maintained by a temperature control unit 30, wherein said temperature control unit 30 is any device known to one skilled in the art and has the capacity to maintain a temperature between 0-100° C. within ±2° C. fluctuations. Shear device 40 is configured to be in fluid communication (at outlet 210 in FIGS. 1A and 1B) with vessel 50, wherein said fluid communication may be any as known to one skilled in the art. The temperature of vessel 50 is maintained by a temperature control unit 30, wherein said temperature control unit 30 is any device known to one skilled in the art and has the capacity to maintain a temperature between 0-100° C. within ±2° C. fluctuations. In some embodiments, a pump 45 is included to control the flow into vessel 50. Pump 45 is configured for either continuous or semi-continuous operation, and may be any suitable pumping device. In some cases, processed therapeutic fluid 55 is administered to a patient via a catheter intravenously. The method of administering processed therapeutic fluid 55 to a patient may be any known to one skilled in the art, such as intravenous injection, intravenous infusion, or intramuscular injection.

Advantages. In some embodiments, the application of shear is especially useful in creating therapeutic dispersions/fluids wherein the therapeutic agents (drugs) are not miscible or soluble in the continuous phase. For example, ozone as a therapeutic gas is dispersed in phosphate buffer saline (PBS) into gas bubbles that are on the nano or sub-nano scale. When such dispersions are injected or infused into patients, ozone gas is circulated in the bloodstream and transported to various organs and tissues. Because the size of the produced gas bubbles are small (nano-, sub-nano-size), ozone gas has the potential to overcome the blood brain barrier (BBB) to obtain access to the brain and therefore become effective therapeutically.

Many other kinds of drugs have low solubility in aqueous solution in the range of room temperature and body temperature. In the same principle as the ozone therapy example, the application of shear stress can create dispersions of such therapeutics, make them administrable to patients, and increase their therapeutic efficacy. Some examples are but not limited to anti-inflammatory drugs (e.g., ibuprofen, acetaminophen), anti-cancer drugs (doxorubicin, paclitaxel, 5-fluorouracil), and anti-HIV drugs (e.g., azodicarbonamide). When drugs are dispersed in fluids to nano- and sub-nanosizes, they can escape being captured by the reticuloendothelial system (RES) and reach the target drug action site via blood circulation.

The fine dispersion of the drug combined with passage through the shear device allows for better absorption of drugs into the cells and tissues, thus making the drugs more effective and reducing adverse effects the drugs have on the liver. This also reduces the amount of drugs required because the liver is not filtering out the drugs. In some cases, the application of shear activates chemotherapy drugs by creating free radicals. These radicals are capable of destroying cancer cells. Thus the application of shear increases the efficacy of the chemotherapy drugs.

In an embodiment, applying shear to a drug-containing therapeutic fluid causes a non-administrable drug to become available for administration (such as hydrophobic drugs, therapeutic gases) because such drugs become well-dispersed in and intimately-mixed with the fluid in their nano-size equivalents after being subjected to shear processing. In an embodiment, applying shear to a drug-containing therapeutic fluid increases the bioavailability of the drug. In another embodiment, applying shear to a drug-containing therapeutic fluid changes the pharmacokinetics and/or pharmacodynamics of the drug. For example, drug absorption, distribution, and/or elimination are changed to improve drug efficacy and safety.

Drug-Loaded Carriers

In an embodiment, as illustrated by FIG. 3A, a therapeutic fluid containing a drug is processed in a shear device together with a drug carrier. The drug and the drug carrier are subjected to a suitable shear rate for a period of time so that the processed therapeutic fluid after exiting the shear device contains the carrier loaded/incorporated with the drug. The loading/incorporation of the drug into the drug carrier may be via any suitable mechanism (such as chemical or physical bonding, absorption) depending on the type of the drug and the carrier.

The shear rate generated in high shear device (HSD) may be in the greater than 20,000 s$^{-1}$. In some embodiments the shear rate is at least 40,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s−1. In some embodiments the shear rate is at least 1,600,000 s$^{-1}$. In embodiments, the shear rate generated by HSD is in the range of from 20,000 s−1 to 100,000 s$^{-1}$. For example, in one application the rotor tip speed is about 40 m/s (7900 ft/min) and the shear gap width is 0.0254 mm (0.001 inch), producing a shear rate of 1,600,000 s−1. In another application the rotor tip speed is about 22.9 m/s (4500 ft/min) and the shear gap width is 0.0254 mm (0.001 inch), producing a shear rate of about 901,600 s$^{-1}$.

In some embodiments, the processed therapeutic fluid is immediately administered to a patient via any suitable means known to one skilled in the art. In some other embodiments, the processed therapeutic fluid is stored. In some further embodiments, the processed therapeutic fluid is further processed.

Selection of the shear device, shear rate, shear stress, and residence time applied in shear device also depends on the amount of therapeutic fluid/dispersion, the type and amount of drug, the type and amount of drug carrier utilized.

Drug Carrier

Drug carriers are often used to (1) increase the drug bioavailability at target site; (2) reduce the toxic side effects of drugs for normal tissues; (3) reduce drug degradation before it reaches the desired site of action. Drug carriers (or drug delivery systems/vehicles) are designed to achieve the above effects by (1) encapsulating drugs inside and thus providing them protection before they reach the desired site of action; (2) changing the size and molecular weight of the "effective drugs" and thus optimizing their biodistribution and pharmacokinetics; and (3) utilizing various targeting schemes and thus minimizing the side effects to normal/healthy tissues. For example, hydrophobic drugs, which are not soluble in the blood and do not reach their target site, can thereby be administered via the use of a suitable carrier. Such suitable carriers include small molecules, proteins, and large DNA fragments.

Generally speaking, drug carriers comprise polymer-based systems, liposomes and lipid nanoparticles, viral vectors and virus-like particles, nanofibers, and inorganic nanoparticles with sizes ranging from nanometers to microns.

Polymer-Based Systems

Polymeric nanoparticles. Polymers offer great flexibility as delivery systems in terms of their synthesis and preparation methods, types of agents that can be encapsulated, and their versatility (e.g., biocompatibility, biodegradability, surface modifiability). Some natural polymers that have been used to construct delivery systems are: albumin, gelatin, alginate, collagen, and chitosan. A few examples of synthetic polymers are: poly lactic acid (PLA), poly glycolic acid (PGA), their copolymers poly lactide-co-glycolide (PLGA), polyacrylates, poly caprolactone (PCL), and polyethylene oxide (PEO). The methods used to prepare polymeric nanoparticles include single (oil-in-water) emulsion, double emulsion (water-in-oil-in-water), emulsification solvent diffusion method, self-assembly, etc. The drug release profile from the polymeric nanoparticles can be modulated by polymer/drug properties and external conditions such as pH, temperature, and magnetic field.

A classic representation of polymeric nanoparticles as versatile delivery systems can be seen in the case of polymeric micelles. Micelle core formation can be driven by different forces (e.g., hydrophobic interactions, electrostatic interactions); micelle shell often serves for biocompatibility and steric stabilization; the surface of the micelles can be modified to include targeting moieties, (e.g., peptides, antibodies). The wide variety of tunable parameters of polymeric nanoparticles has enabled them to be used as delivery systems in numerous biomedical applications. A few of the most important applications are cancer chemotherapy, drug delivery to brain, and gene delivery.

Dendrimers. Dendrimers are highly branched macromolecules with repeated units. The first dendrimers were synthesized by Vögtle in 1978 with "a divergent method", followed by others such as Tomalia. In 1990 Fréchet introduced the "convergent" approach to synthesize well-defined dendritic molecular architectures. Since then, dendrimers have drawn tremendous attention due to their unique molecular architecture. Some of their outstanding features are: (1) highly branched structures giving rise to multivalency, (2) well-defined molecular weight with low polydispersity index, (2) tunable core structure and folding branches creating cavities of hydrophilic or hydrophobic nature, and (3) surface groups amenable for modification for desired applications. As a result, delivery systems formed by dendrimers have well-controlled size, shape, density, polarity, reactivity, and solubility. Bioactive agents can be incorporated by being encapsulated into the dendrimer core or chemically attached or physically adsorbed onto the dendrimer surface.

Among more than 50 families of dendrimers, poly amidoamine (PAMAM) dendrimers are the first that are synthesized, characterized, and commercialized. PAMAM has been utilized to incorporate and to deliver genes, anti-tumor drugs (e.g., 5-fluorouracil), anti-inflammatory drugs (e.g., ketoprofen), and antimalarials drugs (e.g., artemether).

Nanogels. Nanogels are networks of polymeric particles formed by cross-linking, whose size is in the submicron range. Nanogels can be prepared by two different methods: (1) emulsion polymerization and (2) cross-linking of pre-formed polymer fragments. Emulsion polymerization is the most commonly used method for nanogel preparation, but because the polymerization takes place in a mixture (usually an emulsion) of monomers, cross-linking agents, and surfactants, the final products are often toxic and not suitable for biomedical applications unless purified after the synthesis.

The advantages of using nanogels as drug delivery systems are their high drug loading capacity and their ability to respond reversibly to change in external conditions, e.g., temperature, pH, ionic strength, and solvent property. Temperature-responsive nanogels are mostly constructed by poly N-isopropylacrylamide (PNIPAAm) and its derivatives. The mechanism is based on polymer phase separation phenomenon that occurs when the temperature is raised to its lower critical solution temperature (LCST), above which nanogels tend to shrink/collapse and below which they are swollen. These nanogels have manifested controlled and sustained release of drug when subject to temperature changes.

PH-sensitive nanogels made of poly methacrylic acid-grafted-ethylene glycol [P(MAA-g-EG)] have been used for protein delivery. Insulin have been incorporated into P(MAA-g-EG) nanogels and tested via oral administration. In an acidic environment like that of the stomach, the gels are not swollen because of the formation of intermolecular complexes, protecting insulin from degradation by proteases. In basic and neutral environments like the intestine, the intermolecular complexes dissociate, causing rapid gel swelling and consequent insulin release. Other examples include glucose-sensitive nanogels, gene delivery, and anti-tumor drug delivery.

Liposomes and Lipid Nanoparticles

Liposomes and lipid nanoparticles are spherical vesicles, whose membrane is composed of phospholipid bilayer. They can be made by different methods, e.g., extrusion, reversed-phase evaporation, detergent-based procedures, high pressure homogenization, micro-emulsion method, high speed stirring and/or ultrasonication, water-oil-water double emulsion method, solvent emulsification evaporation/diffusion.

Liposomes are another type of drug carriers. There are four mechanisms of liposome-cell interactions: (1) adsorption, (2) endocytosis, (3) fusion, and (4) lipid exchange. Liposomes have great flexibility with regard to their size, structure, composition, and modification. Bioactive agents can be encapsulated in the aqueous environment of the lipid bilayer vesicle (e.g., hydrophilic drugs and DNA). Lipid-soluble drugs can be solubilized in the lipid bilayer. Surface modifications can prevent them from being captured by the reticuloendothelial system (RES). Homing peptides can help them to actively target pathological tissues for diagnosis and treatment of diseases. Unmodified liposomes are preferentially taken up by the RES; therefore they have been used to encapsulate drugs with toxic side effects and to passively target the RES. An example is the use of antibiotic amphotericin B to treat systemic fungal infections. Amphotericin B has extensive renal toxicity; whereas liposomal amphotericin B (Ambisome) reduces the renal toxicity of the drug at normal doses while treating the liver and spleen by passive targeting. Other applications include using liposomes to enhance immunological response (immunoadjuvants), to deliver genes into specific cells in the body, and to deliver active agents to brain.

Viral Vectors and Virus-Like Particles

Another category of delivery systems is viral vectors and virus-like particles, which are designed to mimic viral behavior in infecting cells. Viruses are very efficient in transfecting their own DNA into specific host cells and use the machinery of the host cells to reproduce themselves. This behavior is ideal in drug or gene delivery, but because viruses are pathogenic, they must be used in modified forms. Recombinant viral vectors and virus-like particles (VLPs) are such modified delivery systems.

Recombinant viral vectors. A recombinant viral vector is designed to retain the efficiency of gene transfer and expression but to eliminate the pathogenicity of the virus. The non-essential genes of the viruses (for their replication phase) are replaced by foreign genes of interest so as to disable the innate viral infection in the host. But the modified viruses are still capable of transfecting the desired cell types with the foreign genes of interest and induce gene expression in the host.

There are many different types of recombinant viral vectors, e.g., adenovirus vectors, retrovirus vectors, adeno associated virus vectors, vaccinia virus vectors, herpes simplex virus vectors, etc. Adenovirus vectors contain linear double-stranded DNA's with no envelops. They can be produced cost-effectively and consistently with high infectious ability into both dividing and non-dividing cells. Though they are widely used for gene delivery in vivo and are in clinical trials for cancer therapy, they often stimulate immune response to the cells transfected and thus cause loss of gene expression 1-2 weeks after injection.

Retrovirus vectors are modified from retroviruses that have single-stranded RNA's and envelops, which contain proteins that specifically interact with surface receptors of the target cells. The viral replication genes are replaced with foreign genes of interest. After cell infection, the viral genome is reverse transcribed into double-stranded DNA, integrated into the host genome, and expressed as proteins. Two major advantages of using retroviral vectors in gene delivery are (1) stable long-term integration in the host genome and (2) lowest clinical toxicity. Therefore, they are most suitable for treatment of genetic diseases where permanent gene expression is desirable.

Virus-like particles (VLPs). Unlike recombinant viral vectors, virus-like particles (VLPs) contain no viral genome at all but only the viral capsid proteins so as to mimic the structural confirmation of the actual viruses, which enables them to efficiently transfect cells.

Papilloma VLPs have been used for immune therapy for papilloma virus-related diseases. For example, long-term protection against the rabbit papilloma virus has been stimulated by the papilloma VLPs. In addition, different types of papilloma VLPs have been shown to induce immune responses from B and T lymphocytes and thus demonstrated the potential of using VLPs for immunization against different types of papilloma viruses. Another major category of VLPs is polyoma virus-like particles. By encapsulating plasmid pCMV-β-gal as its genomic information, this system has successfully transfected monkey kidney cell lines and caused consequent expression of functional β-galactosidase. Furthermore, a fluorescent protein and a low molecular weight drug methotrexate have been encapsulated by the polyoma VLPs and delivered into mouse fibroblasts in vitro, giving promise to their applications in not only gene delivery but also delivery of therapeutics and vaccines.

Nanofibers

Nanofibers can be made from carbon, organometallic compounds, inorganic compounds, and polymers. They have a diameter of a few to hundreds of nanometers. Because of the biocompatibility, biodegradability, and ease of formation, polymeric nanofibers are suitable for biomedical applications. As delivery systems, nanofibers have a few outstanding characteristics: (1) large surface area, (2) ease of surface functionalization, and (3) controlled pore size enabling modifiable release kinetics by changing the composition and morphology of the nanofibers. Different methods can be used to produce polymer nanofibers, e.g., drawing, template synthesis, self-assembly, and electrospinning, among which electrospinning is the most attractive method for biomedical applications with the capability of large-scale production.

Nano-fibrous scaffolds containing various growth factors are useful in tissue engineering and have demonstrated controlled release of the growth factors. These results hold promise for bone repair and regeneration and for treating Alzheimer's disease and Parkinson's disease, where peripheral nerve regeneration is needed. Other applications of polymeric nanofibers include the delivery of DNA and small drug molecules (e.g., antibiotic tetracycline hydrochloride, anti-tuberculosis drug rifampin).

Inorganic Nanoparticles

Various inorganic nanoparticles have drawn significant attention in biomedical applications due to their unique structural, spectroscopic, or magnetic properties. They have expanded the armory of nanotechnology as novel diagnostics and therapeutics. Some examples of inorganic nanoparticle types are: (1) carbon nanotubes and fullerenes, (2) quantum dots, (3) nanoshells, (4) gold nanoparticles, and (5) paramagnetic nanoparticles.

Carbon nanotubes and fullerenes. The backbone of carbon nanotubes (CNTs) is composed only of carbon atoms, which are arranged in benzene-ring conformation as graphite sheets. The carbon graphite sheets are then rolled up to form seamless cylinders, which can be either single-walled CNTs or multi-walled CNTs. They are considered to be one of the allotropes of carbon. The structure of fullerenes resembles that of a soccer ball. Their diameter can be as small as 2 nm.

Carbon nanotubes can be produced by three different methods: chemical vapor deposition, electric arc discharge, and laser ablation. After the CNTs are produced, a significant amount of residues are left in the final product. Therefore, purification is necessary for subsequent applications. Various purification techniques include oxidation, chromatography, centrifugation, filtration, and chemical functionalization. Furthermore, because CNTs are completely insoluble in aqueous solutions by themselves, they need to be functionalized in order to be dispersed and stabilized in solution for biomedical applications. Two approaches have been used to modify the CNT surface to increase its solubility—noncovalent and covalent. Suitable noncovalent modifications include the use of polysaccharides, peptides, proteins, and nucleic acids. Covalent modifications include (1) the use of acids to add hydrophilic functional groups to the CNT surface by oxidation and (2) the addition reaction that CNTs undergo to become functionalized CNTs (f-CNTs), which are soluble in various solvents. Functionalized CNTs (f-CNTs) have a few attractive features for biomedical applications: (1) they have large inner volume relative to the tube dimensions, which can be loaded with desired bioactive agents for delivery; they have low toxicity, and (3) they are non-immunogenic. For example, CNTs have been double functionalized with fluorescein and an antibiotic drug (amphotericin B, AmB), which enabled both the tracking of the uptake of CNTs and the delivery of AmB as an antifungal treatment. Other application of CNTs include the delivery of nucleic acids, proteins, and vaccines.

Similar to CNTs, fullerenes can also be functionalized on the surface to become soluble in aqueous solutions. Their hollow structures allow loading of bioactive agents for drug and gene delivery applications. Fullerenes are themselves strong antioxidants. They are capable of removing free radicals that are associated with certain diseases. For example, in neurodegenerative diseases, oxygen free radicals break chemical bonds in critical molecules (e.g., nucleic acids) due to the presence of their unpaired electrons and thus cause cell damage and possible apoptosis. Dugan et. al. showed that carboxylic acid functionalized fullerenes are water soluble and can efficiently scavenge free radicals, which demonstrated their potential in treating neurodegenerative diseases. In the case of cancer treatment, intracellular uptake of fullerene-pyropheophorbide a complexes in Jurkat cells has been reported, in which photo-induced cytotoxicity was observed in culture. Furthermore, fullerene-paclitaxel conjugate was reported to have significant anticancer activity with slow drug release kinetics. Ashcroft et. al. synthesized and characterized a water-soluble fullerene derivative that is covalently attached to an antibody to recognize human tumor cell antigen, which opened up the opportunity of using fullerenes as active targeting delivery systems. Other applications of fullerene derivatives include delivery of antibacterial agents, plasmid DNA, nuclear medicine, and magnetic resonance imaging contrast agents.

Quantum dots. Quantum dots (QDs) are nano-scale semiconductors with many superior optical properties compared to conventional fluorescent dyes. The emission fluorescent spectra of QDs are tunable by changing the composition and size of the QDs. Their spectra have narrow and discreet frequencies from ultraviolet to the infrared range. QDs are very efficient in absorbing and emitting light, making them sensitive light sensors and excellent light emitters. QDs are found to be 10-20 times brighter than organic dyes. QDs are also one order of magnitude more resistant to photobleaching than their organic fluorescent dye counterparts. QDs exhibit cytotoxicity both in vitro and in vivo, which hinders their biomedical applications. But QDs may be modified on the surface with hydrophilic polymers and biological ligands, e.g., antibodies, peptides, oligonucleotides. Therefore, they have the potential to be developed into probes with specific targeting capabilities.

Han et. al. reported the use of well-controlled different-sized QDs embedded in polymeric microbeads for multicolor optical coding in vitro, which can be used for gene expression study, high-throughput screening, and medical diagnostics. Furthermore, Gao et. al. encapsulated semiconductor QDs with an ABC triblock copolymer and linked to a monoclonal antibody that specifically target human prostate cancer cells. This QD-based multifunctional probe demonstrated cancer targeting and imaging abilities in live animals. Other applications of QDs include lung imaging and human breast cancer imaging.

Nanoshells. Similar to quantum dots, nanoshells also have tunable optical properties with emission/absorption spectra expanding from the ultraviolet to the infrared frequencies. They are constructed with a dielectric core (usually silica) with a thin metal shell (typically gold). Nanoshells have no heavy metal in their composition and therefore are not toxic. But their sizes are bigger than QDs, which is the major disadvantage for their biomedical applications.

Nanoshells with polyethylene glycol (PEG) coating have been used in vivo as long-circulating imaging contrast agent with optical coherence tomography and photoacoustic tomography. More interestingly, nanoshells have been designed to serve as photo-absorbers, which can generate effective thermal energy in photo-thermal ablation therapy. AuroShell™ (Nanospectra) particles belong to this nanoshell therapeutic family. After these nanoparticles are delivered to neoplastic tissues, a near-infrared laser light is illuminated externally at the tumor site, AuroShell™ then act as specific heat generators by absorbing the light energy and converting it to heat, thus destroying the cancerous tissues.

Gold nanoparticles. Gold nanoparticles are are easy to fabricate and they can strongly absorb and scatter light at desired wavelengths. Gold nanoparticles are less toxic compared to quantum dots and the metal gold is approved by FDA for some therapeutic applications. Copland et. al. conjugated gold nanoparticles to a monoclonal antibody to target human breast cancer cells. The in vitro experiments demonstrated efficient selective targeting and imaging by optoacoustic tomography of human SK-BR-3 breast cancer cells in a gelatin phantom that optically resembled breast tissue. The limit of detection concentration at a depth of 6 cm was 109 nanoparticles per ml. Paciotti et. al. developed a gold nanoparticle based drug delivery system that has attached PEG and recombinant human tumor necrosis factor on its surface. In vivo animal tests showed that these nanoparticles, after intravenous administration, rapidly accumulated in colon carcinomas but not in the livers, spleens, or healthy organs, indicating that the particles escaped the RES system and had selective targeting ability. The system was further developed to include paclitaxel as a multifunctional nano-scale delivery platform. Gold nanoparticles are further used in radiotherapy, vital reflectance imaging, and photo-thermal cancer therapy.

Paramagnetic nanoparticles. Paramagnetic nanoparticles have been utilized alongside with the fast advancement of MRI. MRI has 3D high spatial resolution as its advantage but lower sensitivity compared to nuclear imaging. The successes of utilizing MRI for diagnosis and therapy assessment depend to a large extend on the contrast-to-noise ratio obtainable, which necessitates the use of contrast agents, e.g., gadolinium-based conjugates, iron oxide nanoparticles. Iron oxide nanoparticles have attracted much attention because of their superparamagnetic property (i.e., high magnetic susceptibility) that enables them to produce substantially high contrast.

Ultra-small superparamagnetic iron oxide (USPIO) has been found to be small enough to migrate across the capillary wall via vesicular transport and through inter-endothelial junctions [202]. There have been numerous applications of this class of nanoparticles in conjunction with both passive and active targeting strategies. In the case of passive targeting, USPIO has been used for MRI of cardiovascular diseases, MRI of the lymphatic system and associated cancers and metastases, MRI of arthritis, MRI of transplanted pancreatic islets, etc. For active targeting, iron oxide nanoparticles have been conjugated to different targeting moieties (e.g., antibodies, peptides) to detect cancers, atherosclerotic plaques where apoptosis takes place, and even in combination with delivery of chemotherapeutic drugs. There also have been several commercialized iron oxide nanoparticles for cancer diagnosis, e.g., ferumoxtran-10, AMI-227, and Combidex® developed by Advanced Magnetics Inc., and Sinerem® by Laboratoire Guerbet.

Figure 3B:
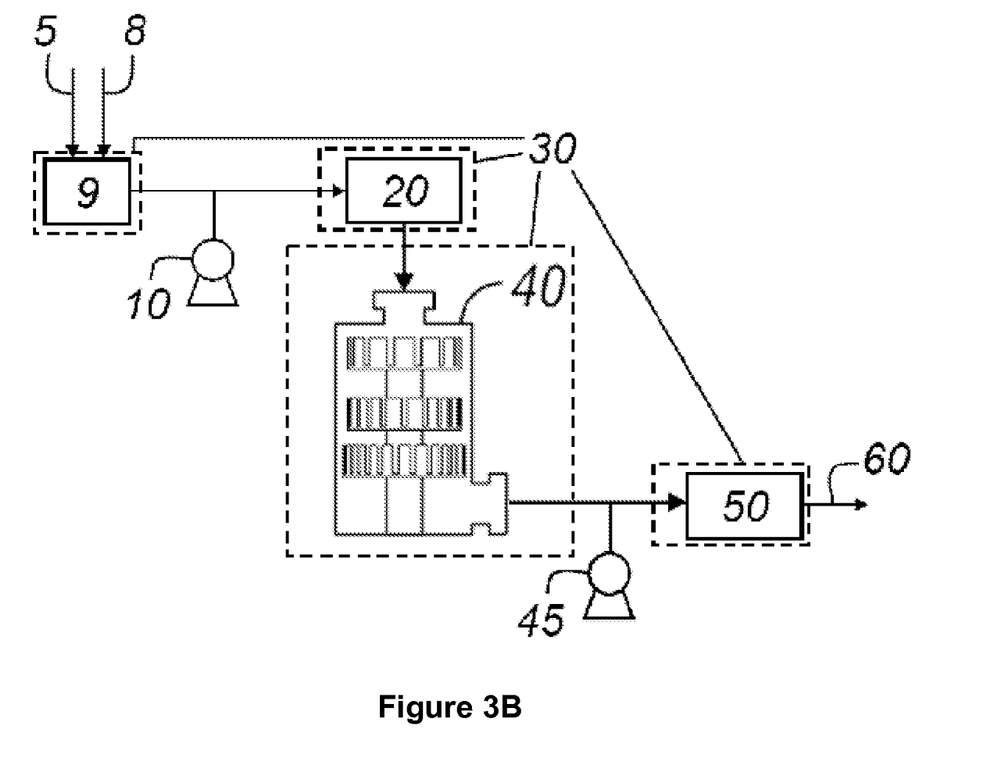
FIG. 3B is a process flow diagram demonstrating the application of shear stress in conjunction with a drug carrier for drug delivery.

Referring to FIG. 3B, a drug carrier 8 is mixed with a therapeutic fluid 5 in vessel 9 with a temperature control unit 30. The temperature control unit 30 is any device known to one skilled in the art and has the capacity to maintain a temperature between 0-100° C. within ±2° C. fluctuations. In alternative embodiments, mixing vessel 9 is omitted. Mixing vessel 9 is configured to be in fluid connection with vessel 20. In some embodiments, the temperature of vessel 20 is maintained by a temperature control unit 30. The temperature control unit 30 is any device known to one skilled in the art and has the capacity to maintain between 0-100° C. within ±2° C. fluctuations.

In some embodiments, a pump 10 is included to control the flow into vessel 20. Pump 10 is configured for either continuous or semi-continuous operation, and may be any suitable pumping device. Vessel 20 is configured to be in fluid connection with shear device 40 (at inlet 205 in FIGS. 1A and 1B), wherein said fluid connection may be any as known to one skilled in the art. The temperature of shear device 40 is maintained by a temperature control unit 30, wherein said temperature control unit 30 is any device known to one skilled in the art and has the capacity to maintain a temperature between 0-100° C. within ±2° C. fluctuations. Shear device 40 is configured to be in fluid connection (at outlet 210 in FIGS. 1A and 1B) with vessel 50, wherein said fluid connection may be any as known to one skilled in the art. The temperature of vessel 50 is maintained by a temperature control unit 30, wherein said temperature control unit 30 is any device known to one skilled in the art and has the capacity to maintain a temperature between 0-100° C. within ±2° C. fluctuations. In some embodiments, a pump 45 is included to control the flow into vessel 50. Pump 45 is configured for either continuous or semi-continuous operation, and may be any suitable pumping device. In some cases, processed therapeutic fluid 60 containing drug-loaded carrier is administered to a patient. The method of administering processed therapeutic fluid 60 may be any known to one skilled in the art, such as intravenous injection.

Advantages. In some embodiments, the application of shear in creating a drug-loaded carrier fully utilizes the features of the drug carrier, some of which are discussed above; it also improves the loading capacity of the drug carrier, thus reducing the amount of drug and carrier wasted. For example, the application of shear reduces the size of the drug and causes it to be more efficiently packaged within a suitable drug carrier. In some cases, the amount of drug loaded into a drug carrier per weight of the carrier is increased by the application of shear. In some other cases, a suitable interaction is created between an otherwise non-loadable drug and a drug carrier by utilizing shear, thus making the drug-carrier incorporation possible. In yet other cases, the interaction between the drug and the carrier is enhanced by the application of shear, thus causing the drug to be incorporated into the carrier more efficiently.

Drug-Loaded Carriers and Modification

In an embodiment, as illustrated by FIG. 4A, a therapeutic fluid containing a drug is processed in a shear device together with a drug carrier. The drug and the drug carrier are subjected to a suitable shear rate for a period of time so that the processed therapeutic fluid after exiting the shear device contains the carrier loaded/incorporated with the drug. In some embodiments, the processed therapeutic fluid containing the drug-loaded carrier is concentrated. In some cases, the drug-loaded carrier is extracted or purified from the processed therapeutic fluid. The drug-loaded carrier is then further modified with a targeting moiety to constitute targeted drug delivery.

In some embodiments, the modified drug-loaded carrier is immediately administered to a patient via any suitable means known to one skilled in the art. In some other embodiments, the modified drug-loaded carrier is stored. In some further embodiments, the modified drug-loaded carrier is further processed.

Targeting Moiety

The targeting moiety utilized to modify (e.g., surface modification) the drug-loaded carrier may be any known to one skilled in the art. Some examples are antibodies, peptides, polypeptides, nucleic acids, DNA, RNA, and their fragments. This disclosure includes targeting moieties that are natural, isolated, or synthetic. The targeting moieties may be used in multivalency or single valency per drug carrier. The method for achieving carrier modification is any suitable means known to one skilled in the art.

Advantages. In some embodiments, the application of shear in creating a modified drug-loaded carrier fully utilizes the features of the modified drug carrier; it also improves the loading capacity of the drug carrier, thus reducing the amount of drug, carrier, and targeting moiety wasted. For example, the application of shear reduces the size of the drug and causes it to be more efficiently packaged within a suitable drug carrier. In some cases, the amount of drug loaded into a drug carrier per weight of the carrier is increased by the application of shear. In some other cases, a suitable interaction is created between an otherwise non-loadable drug and a drug carrier by utilizing shear, thus making the drug-carrier incorporation possible. In yet other cases, the interaction between the drug and the carrier is enhanced by the application of shear, thus causing the drug to be incorporated into the carrier more efficiently. In targeted delivery, especially for cancer treatment, these advantages reduce the amount of drug a patient needs, thus reducing potential side effects.

While preferred embodiments of the invention have been shown and described, modifications thereof can be made by one skilled in the art without departing from the spirit and teachings of the invention. The embodiments described herein are some only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide some, procedural or other details supplementary to those set forth herein.

What is claimed is:

1. A method comprising
subjecting a therapeutic fluid containing a drug to high shear of at least 20,000 s$^{-1}$ that is generated by a high shear device having at least one rotor/stator that are separated by a shear gap; and
obtaining a processed therapeutic fluid, wherein the processed therapeutic fluid contains the drug in sub-nano size.

2. The method of claim 1 wherein said drug is in the form of a solid, liquid, gas, solution, gel, emulsion, powder, or a combination thereof.

3. The method of claim 1 further comprising controlling the shear rate that the therapeutic fluid is subjected to high shear.

4. The method of claim 1 further comprising controlling the period of time that the therapeutic fluid is subjected to high shear.

5. The method of claim 1 wherein subjecting the therapeutic fluid containing said drug to high shear comprises creating free radicals of the drug.

6. A method comprising
subjecting a drug carrier and a therapeutic fluid containing a drug to high shear of at least 20,000 s$^{-1}$ that is generated by a high shear device having at least one rotor/stator that are separated by a shear gap, maintaining the temperature between 1° C. and 100° C.±2° C. during shearing; and
obtaining a processed therapeutic fluid, wherein the processed therapeutic fluid contains the drug carrier loaded with the drug in sub-nano size.

7. The method of claim 6 further comprising administering the processed therapeutic fluid to a patient.

8. The method of claim 6 wherein subjecting said drug carrier and the therapeutic fluid containing said drug to high shear creates an interaction between the drug carrier and the drug or enhances the interaction between the drug carrier and the drug.

9. The method of claim 6 wherein subjecting said drug carrier and the therapeutic fluid containing said drug to high shear improves the loading capacity of the drug carrier for the drug.

10. A method comprising
applying high shear to a drug carrier and a therapeutic fluid containing a drug, wherein the high shear is of at least 20,000 s$^{-1}$ that is applied by a high shear device having at least one rotor/stator that are separated by a shear gap of less than about 5 mm;
obtaining a processed therapeutic fluid, wherein the processed therapeutic fluid contains the carrier loaded with the drug in sub-nano size; and
modifying the drug-loaded carrier with a targeting moiety to obtain a modified drug-loaded carrier.

11. The method of claim 10 further comprising concentrating the processed therapeutic fluid containing the drug-loaded carrier.

12. The method of claim 10 further comprising purifying the drug-loaded carrier from the processed therapeutic fluid.

13. The method of claim 10 further comprising administering the modified drug-loaded carrier to a patient.

14. The method of claim 10 wherein the modified drug-loaded carrier is used to treat cancer patients.

15. The method of claim 1, wherein the shear gap is in the range of from about 0.02 mm to about 5 mm, and wherein the high shear device operates at a tip speed greater than about 23 m/s.

16. The method of claim 6, wherein the shear gap is in the range of from about 0.02 mm to about 5 mm, and wherein the high shear device operates at a tip speed greater than about 23 m/s.

17. The method of claim 6, wherein the high shear device has an energy expenditure greater than 1000 W/m$^3$.

18. The method of claim 10, wherein the high shear device has an energy expenditure greater than 1000 W/m$^3$.

* * * * *